United States Patent
Gobbi et al.

(10) Patent No.: US 9,363,995 B2
(45) Date of Patent: Jun. 14, 2016

(54) USE OF DERIVATIVE COMPOUNDS OF 1,3-BENZODIOXOLE IN INSECTICIDAL COMPOSITIONS

(71) Applicant: ENDURA S.P.A., Bologna (IT)

(72) Inventors: Carlotta Gobbi, Ravenna (IT); Valerio Borzatta, Bologna (IT); Elisa Capparella, Ravenna (IT)

(73) Assignee: Endura S.P.A., Bologna (IT)

( * ) Notice: Subject to any disclaimer, the term of this patent is extended or adjusted under 35 U.S.C. 154(b) by 0 days.

(21) Appl. No.: 14/385,234

(22) PCT Filed: Mar. 14, 2013

(86) PCT No.: PCT/EP2013/055224
§ 371 (c)(1),
(2) Date: Sep. 15, 2014

(87) PCT Pub. No.: WO2013/135806
PCT Pub. Date: Sep. 19, 2013

(65) Prior Publication Data
US 2015/0038465 A1    Feb. 5, 2015

(30) Foreign Application Priority Data
Mar. 15, 2012    (IT) .............. MI2012A0404

(51) Int. Cl.
*A01N 43/30* (2006.01)
*A01N 57/16* (2006.01)
*A01N 47/22* (2006.01)
*A01N 47/10* (2006.01)
*A01N 25/32* (2006.01)
*A01N 53/00* (2006.01)

(52) U.S. Cl.
CPC .............. *A01N 25/32* (2013.01); *A01N 43/30* (2013.01); *A01N 47/10* (2013.01); *A01N 53/00* (2013.01); *A01N 57/16* (2013.01)

(58) Field of Classification Search
CPC ....... A01N 43/30; A01N 57/16; A01N 47/22; A01N 47/10
USPC ......................................................... 549/234
See application file for complete search history.

(56) References Cited

U.S. PATENT DOCUMENTS 2,485,681 A * 10/1949 Wachs .......................... 549/445
2,550,737 A * 5/1951 Wachs ............................ 514/67
2007/0231413 A1  10/2007 Matsuo et al.

FOREIGN PATENT DOCUMENTS

EP       0512379 A1    11/1992

OTHER PUBLICATIONS

Ugolini et al., "Benzodioxole Derivatives as Negative Effectors of Plant Proteases," Journal of Agricultural and Food Chemistry 53(19): 7494-7501 (2005).
Alexander et al., "Synthesis of Methylenedioxyphenyl Compounds From Isosafrole and Sesamol," Journal of Organic Chemistry 24:1504-1507 (1959).
International Search Report and Opinion for PCT/EP2013/055224, mailed Jul. 3, 2013.
International Preliminary Exam Report for PCT/EP2013/055224, mailed Jun. 27, 2014.

* cited by examiner

*Primary Examiner* — Erich A Leeser
(74) *Attorney, Agent, or Firm* — LeClairRyan, a Professional Corporation

(57) ABSTRACT

The invention relates to the use of a derivative compound of 1,3-benzodioxole of formula (I) wherein R is a linear or branched $(C_4-C_{10})$alkyl substituent as a synergistic compound of insecticidal active ingredients insecticidal compositions comprising at least one compound of Formula (I) and at least one insecticidal active ingredient are also described.

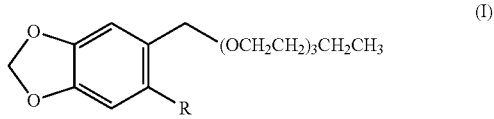

15 Claims, No Drawings

USE OF DERIVATIVE COMPOUNDS OF 1,3-BENZODIOXOLE IN INSECTICIDAL COMPOSITIONS

This application is a national stage application under 35 U.S.C. §371 of PCT Patent Application Serial No. PCT/EP2013/055224, filed Mar. 14, 2013, which claims the priority benefit of Italy Patent Application No. MI2012A000404, filed Mar. 15, 2012.

FIELD OF THE INVENTION

The present invention relates to the use of derivative compounds of 1,3-benzodioxole in insecticidal compositions.

BACKGROUND OF THE INVENTION

It is known that the action of insecticides decreases over time due to resistance phenomena of the insects on account of their developed ability to strengthen their natural defences. A solution to the problem of resistance consists of increasing the dosage of the insecticide so as to restore the action itself; however, this solution is negative in two aspects linked to the increased resistance induced and to the environmental pollution resulting from the high dosages used. Another possible solution is linked to the rotation of insecticides with the same mechanism of action, but with the risk of seeing the development of cross-resistance phenomena.

There have therefore been proposed substances, which by acting on the enzyme systems of the insects, can restore the sensitivity to insecticides, by reducing or eliminating the resistance phenomena and are furthermore capable to increase the sensitivity of the insects themselves even in the case in which there are no resistance phenomena thus contributing to, in any case, lowering the doses of the insecticides used. These products are known as synergists and include derivatives of 1,3-benzodioxole, in particular piperonyl butoxide (also known as PBO),

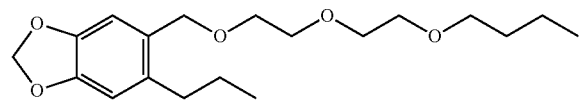 [SMILES: CCCCOCCOCCOCc1cc2c(cc1CCC)OCO2]

5-[2-(2-butoxyethoxy)-ethoxymethyl]6-propyl-1,3-benzodioxole, is known to be a powerful synergist for insecticides, in particular in respect of pyrethrins, pyrethroids, insect growth regulators (IGR), carbamates, organic phosphorus compounds and, recently, also neonicotinoids and other insecticides such as, for example, those of the METI (Mitochondrial electron transport inhibitors) class.

In order to further and significantly improve the insecticidal action of the final formulations, above all for use in the presence of resistance phenomena, there have also been proposed formulations of insecticides and piperonyl butoxide both as complexes in cyclodextrins and microencapsulated in microcapsules made of polymer material. For this latter formulation, the piperonyl butoxide acts immediately on the enzyme systems of the insects, restoring the sensitivity thereof so that the insecticide released after some time may carry exercise its action.

In view of the synergistic action of the piperonyl butoxide there were proposed derivatives of the 1,3-benzodioxole as alternative products for the synergistic action in the insecticidal compositions.

In U.S. Pat. No. 7,354,911 there are described derivative compounds of 1,3-benzodioxole of formula

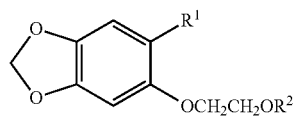

Wherein $R^1$ is an alkyl group or a $C_3$ alkenyl group and $R^2$ is a $C_1$-$C_3$ alkyl group. In WO 2011/020848 compounds of formula (I) are described:

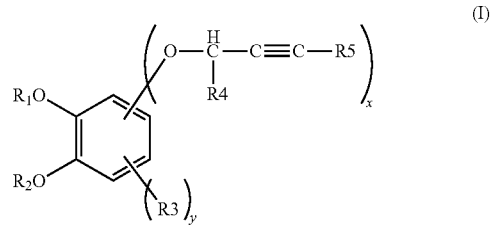

Among the various meanings of $R_1$, $R_2$ and $R_3$, there is highlighted the fact that $R_1O$— and $R_2O$— taken together can represent a —O—$CH_2$—O— group or a benzodioxole group and that R3 is a ($C_1$-$C_6$)alkyl and y is 0, 1 or 2. These compounds are proposed as synergists of insecticidal active ingredients, in particular of the class of pyrethroids.

It is still felt the need to provide additional synergistic products to be employed with insecticidal active ingredients.

SUMMARY OF THE INVENTION

The invention therefore relates to the use of a derivative compound of 1,3-benzodioxole of formula (I).

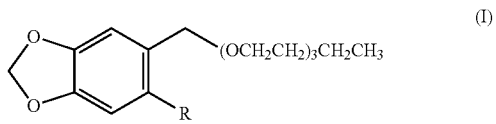

wherein R is a linear or branched ($C_4$-$C_{10}$)alkyl substituent as a synergistic compound of insecticidal active ingredients.

In another aspect, the invention therefore relates to an insecticidal composition comprising at least one insecticidal active ingredient and at least one synergistic compound of formula (I).

Under a further aspect, the invention relates to the following compounds:
a) 5-[2-(2-butoxyethoxy)-ethoxymethyl]-6-n-octyl-1,3-benzodioxole)

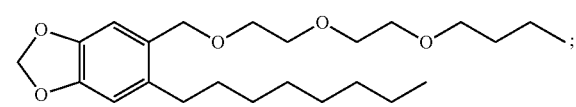 [SMILES: CCCCCCCCc1cc2c(cc1COCCOCCOCCCC)OCO2]

compound of Formula (I) wherein R is an n-octyl substituent
b) 5-[2-(2-butoxyethoxy)-ethoxymethyl]-6-n-decyl-1,3-benzodioxole)

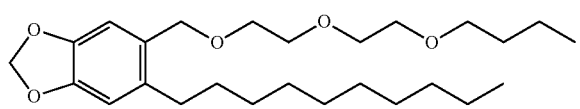 [SMILES: CCCCCCCCCCc1cc2c(cc1COCCOCCOCCCC)OCO2]

In yet a further aspect of the invention, the invention relates to the use of the insecticidal composition as insecticide.

In yet a further aspect of the invention, the invention relates to the insecticidal composition of the invention for use in veterinary medicine.

In yet a further aspect of the invention, the invention relates to the insecticidal composition for use in treating pediculosis in humans.

DETAILED DESCRIPTION OF THE INVENTION

The invention therefore relates to the use of a derivative compound of 1,3-benzodioxole of formula (I)

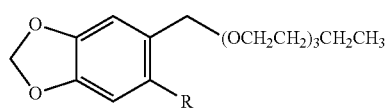

wherein R is a linear or branched ($C_4$-$C_{10}$)alkyl substituent as a synergistic compound of insecticidal active ingredients.

In another aspect, the invention therefore relates to an insecticidal composition comprising at least one insecticidal active ingredient and at least one synergistic compound of formula (I).

R is a linear or branched $C_4$-$C_{10}$ alkyl substituent, preferably R is selected from the linear $C_4$-$C_{10}$ group consisting of n-butyl, n-hexyl, n-octyl and n-decyl, more preferably R is an n-octyl or n-hexyl.

Preferably the insecticidal products to be employed in the composition of the invention are insecticides that belong to the following families:

Pyrethroids such as, for example, allethrin, d-allethrin, tetramethrin, d-tetramethrin, prallethrin, phenothrin, d-phenothrin, esbiotrine, imiprothrin, resmethrin, bioresmethrin, metofluthrin, permethrin, cyfluthrin and isomers thereof, cypermethrin and isomers thereof, deltamethrin, ciphenothrin, cyhalothrin and isomers thereof, flumethrin, etofenprox, fenvalerate, esfenvalerate, fenpropathrin, silafluofen, bifenthrin, transfluthrin, tau-fluvalinate, tefluthrin, acrinathrin, empenthrin, 2,3, 5,6-tetrafluoro-4-benzyl(E/Z)-(+/−)-3-(buta-1,3-dienyl)-2,2-dymethylcyclopropane, 2,3,5,6-tetrafluorobenzyl-(1R,3R)-3((E)-buta-1,3-dienyl)-2,2-dimethylcyclopropane-1-carboxylate, 2,3,5,6-tetrafluorobenzyl-(E/Z)-(1R,3R)-3-(buta-1,3-dienyl)-2, 2-dimethylcyclopropane, 2,3,5,6-tetrafluorobenzyl-(E/Z)-(+/−)-3-(hexa-1,3,5-tri-enyl)-2,2-dimethylcyclopropane, pyrethrum, extracts thereof and mixtures thereof;

Organic phosphorous compounds such as, for example, dichlorvos, fenitrothion, cyanophos, profenofos, sulprofos, phenthoate, chlorpyrifos, diazinon, acephate, terbufos, fosthiazate, ethoprophos, cadusafos;

Carbamates such as, for example, propoxur, carbaryl, metoxadiazone, fenobucarb, methomyl, alanicarb, benfuracarb, oxamyl, aldicarb;

Benzoylphenylureic derivates such as, for example, lufenuron, diflubenzuron, triflumuron, teflubenzuron, flufenoxuron, fluazuron, novaluron, triazuron;

Insect growth regulators such as, for example, pyriproxyfen, methoprene, hydroprene, fenoxycarb;

Neonicotinoids such as, for example, acetamiprid, imidacloprid, nitenpyram, thiacloprid, thiamethoxam, clothianidin, dinotefuran;

Phenylpyrazole derivatives such as, for example, acetoprole and ethiprole;

Benzoylhydrazine derivates such as, for example, tebufenozide, methoxyfenozide, halofenozide;

Other insecticides such as, for example, diafenthiuron, pymetrozine, flonicamid, triazamate, buprofezin, spinosad, emamectin benzoate, chlorfenapyr, indoxacarb, pyridalyl, cyromazine, fenpyroximate, tebufenpyrad, piridaben, pirimidifen, etoxazole, fenazaquin, dicofol, propargite, abamectin, milbimectina, amitraz, bensultap, endosulfan, spirodiclofen, spiromesifen, amidoflumet, azadirachtin.

One or more of these insecticidal active ingredients can be used with one or more synergistic products of formula (I) for the insecticidal compositions of the present invention.

In the insecticide compositions of the present invention, the compound of formula (I) is comprised in a weight/weight percentage comprised between 0.01% and 98% of the total weight of the composition. In the case in which two or more compounds of formula (I) are used, the above-mentioned percentages by weight are intended to refer to the sum of the compounds of formula (I) overall present in the composition.

In addition to the aforementioned active ingredients, excipients selected from those commonly utilised in the insecticidal compositions can be present. Among these emulsifiers, UV stabilisers, antioxidants and other additives, not specific for the insecticidal action but useful for the specific application, can be cited. Examples of emulsifiers are dodecylbenzene sulphonates, ligninsulphonates, phospholipids, polyethylene glycols. Examples of UV stabilisers are for example 2-hydroxy-4-methoxybenzophenone, 2-hydroxy-4-octoxy-benzophenone, sebacate of 4-hydroxy-2,2,6,6-tetramethylpiperidine, 2-(5-chloro-2H-benzotriazol-2-yl)-6-(1, 1-dimethylethyl)-4-methylphenol. One example of antioxidant is 2,6-di-tert-butyl-1-hydroxy-toluene.

The weight ratio of insecticide to synergist varies from 1:1 to 1:30, the ratio of between 1:2 and 1:10 is preferred, being the ratio between 1:3 and 1:7 particularly preferred.

The composition of the invention also comprises carriers suitable for obtaining the insecticide formulation of the invention.

The insecticidal composition can in fact be produced as a formulation in solid form (e.g., powders, granules), liquid form (solutions, suspensions, emulsions, microemulsions) or together with a gas carrier, by using the sector technologies. The insecticide formulation can also be encapsulated in order to obtain a modulated release over time.

When the composition is used in solid form, the solid carrier is, for example, a finely divided powder or granules of suitable clays such as, for example, kaolin, diatomic soils, bentonite, silica, talc and other inorganic minerals (such as, for example, activated carbon, calcium carbonate), being also possible to select the inorganic materials among the inorganic fertilizers; a substance, such as cotton, silk, wool and cellulose, a synthetic resin, such as, for example, polyethylene, polypropylene, polyesters, polyamides, polybutadienes, polystyrenes, polyacrylates, polymethacrylates, polyacetals, polysulfones, polyetherimides, copolymers thereof and mixtures of polymers and of copolymers; when the composition is used in liquid form, the liquid carrier is, for example, an aliphatic or aromatic hydrocarbon (for example, xylene, toluene, naphthalene, alkylnaftalene, camphor, kerosene, hexane, cyclohexane and mixtures and isomer mixtures thereof), a halogenated hydrocarbon (for example, chlorobenzene, dichloromethane, dichloroethane), an alcohol, such as, for example, methanol, ethanol, isopropanol, butanol, benzyl alcohol, ethylene glycol and mixtures thereof, ethers, for example, diethylene glycol dimethyl ether, diethylene glycol monomethyl ether, propylene glycol monomethyl ether, tetrahydrofuran, dioxane and mixtures thereof, esters, such as, for example, ethyl acetate, butyl acetate, isopropyl myristate, diisobutyl adipate, diisobutyl glutarate, diisobutyl succinate, 2-ethylhexyl lactate and mixtures thereof, ketones such as, for example, acetone, methyl ethyl ketone, methyl isobutyl ketone, cyclohexanone and mixtures thereof N,N-dimethylformamide, N,N-dimethylacetamide, N-methylpyrrolidone and mixtures thereof, alkylidene carbonates such as, for example, propylene carbonate, vegetable oils such as, for example, soya bean oil, rapeseed oil, cottonseed oil, essential vegetable oils such as, for example, orange oil, lemon oil and mixtures thereof and water; when the composition is used in gaseous form, the gas carrier is, for example, butane gas, liquefied petroleum gas (LPG), carbon dioxide.

In a further aspect, the invention relates to the following compounds:
a) 5-[2-(2-butoxyethoxy)-ethoxymethyl]-6-n-octyl-1,3-benzodioxole)

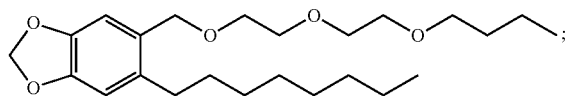 [SMILES: CCCCCCCCc1cc2c(cc1COCCOCCOCCCC)OCO2]

compound of Formula (I) wherein R is an n-octyl substituent
b) 5-[2-(2-butoxyethoxy)-ethoxymethyl]6-n-decyl-1,3-benzodioxole)

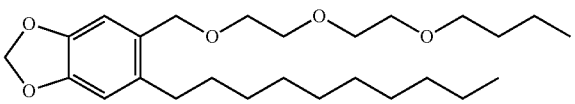 [SMILES: CCCCCCCCCCc1cc2c(cc1COCCOCCOCCCC)OCO2]

In yet a further aspect of the invention, the invention relates to the use of the insecticidal composition as insecticide.

In yet a further aspect of the invention, the invention relates to the insecticidal composition of the invention for use in veterinary medicine.

The invention further includes a method for eliminating insects, characterised by placing the composition of the invention or the formulation of the invention into contact with a substrate containing said infesting organisms, preferably insects. Said substrate can be a closed environment such as, for example, house, schools, barns, offices and other public places, or open environment such as gardens, parks, surfaces for agricultural use; the substrate can also be an object, e.g. tissues, mattresses, carpets containing the infesting organisms; the substrate can be the air present in one of the above-mentioned environments or one of the surfaces that make up said environments.

In yet a further aspect of the invention, the invention relates to the insecticidal composition for use in treating pediculosis in humans.

The composition or formulation of the invention can, therefore, also be applied onto the skin of an animal contaminated by infesting organisms, in particular by insects; in this latter case, the compounds of formula (I) can be applied to the animal directly after appropriate formulation with suitable excipients for veterinary use.

The delivery of the composition of the invention, comprising at least one compound of formula (I) and one insecticidal active ingredient, takes place within the timeframes and in the amounts determined on the basis of the volume of the environment to be treated and of the degree of infestation thereof. Advantageously, the compounds of formula (I) have a low toxicity for humans and animals and can therefore be employed with a wide safety margin.

EXPERIMENTAL PART

Example 1

Synthesis of 5-[2-(2-butoxyethoxy)-ethoxymethyl]-6-n-octyl-1,3-benzodioxole)

A. Synthesis of 5-n-octanoyl-1,3-benzodioxole

In a 500 ml 3-necked reactor equipped with stirring rod, thermometer and reflux condenser, 24.4 g (0.2 moles) of 1,3-benzodioxole in 120 grams of dichloromethane and 5.6 g (0.04 moles) of anhydrous zinc chloride were added at room temperature and in nitrogen stream. The reaction mixture was then added at room temperature and in the time frame of 2 hours with 37.8 g (0.20 moles) of n-octanoyl chloride It was maintained under agitation at room temperature. for 12 hours and then there were added 75 ml of an aqueous solution of NaOH 3M. The organic phase was separated and washed with 70 ml of water, dried on anhydrous sodium sulphate, vacuum filtered and evaporated (25° C./21 mbar). 34 g of dense, oily crude product were obtained, which was used for the successive reaction without further purification.

B. Synthesis of 5-n-octyl-1,3-benzodioxole

Into a 200 ml autoclave there was added a solution obtained by dissolving 34 g of the reaction product A) in 80 ml of isopropanol. To the solution 2.0 g of wet Pd/C 5% 50% were then added. The resulting mixture was then hydrogenated at 75° C. and 5 bar of pressure for 6 hours. It was then cooled and the mixture was filtered on celite to eliminate the catalyst. The filtrate was vacuum concentrated at 25° C./21 mbar. There were obtained 33 g of crude product which were purified by means of chromatography on 400 g of silica, eluting with the n-hexane/isopropyl ether 10/1 (v/v) mixture.

By means of vacuum evaporation of the solvent (25° C./21 mbar) 18.4 g of 5-n-octyl-1,3-benzodioxole with 97.8% titre were obtained, the NMR and MS analyses of which are compliant with the indicated structure.

C. Synthesis of 5-chloromethyl-6-n-octyl-1,3-benzodioxole

Into a 100 ml reactor 17.8 g (0.074 moles) of the previous product, 30.5 ml of HCl conc. and 3.8 g (0.122 moles) of paraformaldehyde and 0.8 g (0.066 moles) of zinc chloride were added. The mixture thus obtained was heated at 60° C. for 6 hours. It was cooled at r.t. The phases were separated and the organic phase (22.2 g) was utilised directly for the subsequent reaction.

D. Synthesis of 5-[2-(2-butoxyethoxy)-ethoxymethyl]-6-n-octyl-benzo[1,3]dioxole

Into a 100 ml reactor at room temperature 23.5 g (0.143 moles) of 2-(2-butoxyethoxy)-ethanol and 4.6 g (0.114 moles) of sodium hydroxide were added. The mixture was agitated at 60° C. for ½ hour, and, then the crude product of the previous reaction was added in 1 hour at 60° C. On termination of the addition it was left under agitation at 60° C. for 1 hour.

After cooling to r.t. there were added 80 ml of dichloromethane. The organic phase was separated, washed with water and dried on anhydrous sodium sulphate. After filtering vacuum concentration (25° C./21 mbar) was carried out, thus obtaining 34 g of crude product, which was purified by chromatography on 400 g of silica, eluting with the n-hexane/isopropyl ether 1/1 (v/v) mixture. After vacuum evaporation of the solvent (25° C./21 mbar) 8.1 g (0.02 moles) of 5-[2-(2-butoxyethoxy)-ethoxymethyl]-6-n-octyl-1,3-benzodioxole (e.g. 201° C./0.8 mbar) as dense colourless oil were obtained by distillation (201° C./0.8 mbar), the NMR and MS analyses of which were compliant with the indicated structure.

Example 2

Synthesis 5-[2-(2-butoxyethoxy)-ethoxymethyl]-6-n-butyl-1,3-benzodioxole)

Analogously as described in example 1 and following the same synthesis method 5-n-butanoyl-1,3-benzodioxole product was prepared by starting from 24.4 g (0.2 moles) of 1,3-benzodioxole and from 21.3 g (0.2 moles) of n-butyroyl chloride. After reduction and subsequent chloromethylation and etherification 27.8 g (0.08 moles) of 5 [2-(2 butoxyethoxy)-ethoxymethyl]-6-n-butyl-1,3-benzodioxole, as dense, colourless oil were obtained by distillation (190° C./0.6 mbar), the NMR and MS analyses of which were compliant with the indicated structure.

Example 3

Synthesis 5-[2-(2-Butoxy-ethoxy)-ethoxymethyl]-6-n-hexyl-1,3-benzodioxole)

Analogously as described in example 1 and following the same synthesis method 5-n-hexanoyl-1,3-benzodioxole product was prepared by starting from 24.4 g (0.2 moles) of 1,3-benzodioxole and from 26.9 g (0.2 moles) of n-hexanoyl chloride. After reduction and subsequent chloromethylation and etherification 23.5 g (0.062 moles) of 5-[2-(2 butoxyethoxy)-ethoxymethyl]-6-n-hexyl-1,3-benzodioxole, as a dense, colourless oil were obtained by distillation (196° C./0.4 mbar), the NMR and MS analyses of which were compliant with the indicated structure Example 4

Synthesis 5-[2-(2-Butoxyethoxy)-ethoxymethyl]-6-n-decyl-1,3-benzodioxole)

Analogously as described in example 1 and following the same synthesis method 5-n-decanoil-1,3-benzodioxole product was prepared by starting from 24.4 g (0.2 moles) of 1,3-benzodioxole and from 38.1 g (0.2 moles) of n-decanoil chloride. After reduction and subsequent chloromethylation and etherification 36.4 g of crude product were obtained, which was purified by chromatography on 400 g of silica with the n-hexane/isopropyl ether 10/1 (v/v) mixture. After vacuum evaporation of the solvent (25° C./21 mbar) 12.8 g (0.03 moles) of 5-[2-(2-butoxyethoxy)-ethoxymethyl]-6-n-decyl-1,3-benzodioxole (e.g. 219° C./0.7 mbar) as a very dense, colourless oil were obtained by distillation (219° C./0.7 mbar), the NMR and MS analyses of which were compliant with the indicated structure.

Example 5

Mortality Test of the Products of Examples 1-4

After having mixed the products of Examples 1-4 with tetramethrin in acetone respectively at a concentration of 1.25% for the products of examples 1-4 and of 0.25% for the tetramethrin, 0.5 μl of acetone solution was applied to adult, female insects of the *Musca domestica* species, on the rear part of the pectoral region. The insect was then transferred to a closed plastic container approximately 12 cm in diameter and 6 cm in height and left at 25° C. with supply of 5% sugar solution. After 24 hours the alive and dead flies were examined to determine the percentage mortality. The total number of flies per container was equal to 20 and the test was repeated three times. For comparison acetone solutions at the same concentrations as previously indicated for the compounds of examples 1-4 and for tetramethrin alone were prepared.

For comparison an acetone solution at an equal concentration of piperonyl butoxide and tetramethrin and an acetone solution at the same concentration of piperonyl butoxide alone were also prepared.

The results obtained are recorded in Table 1:

TABLE 1

| Compound | Conc. Compound (% w/v) | Tetramethrin conc. (% w/v) | Mortality (%) |
|---|---|---|---|
| Ex. 1 | 1.25 | 0 | 0 |
|  | 1.25 | 0.25 | 100 |
| Ex. 2 | 1.25 | 0 | 0 |
|  | 1.25 | 0.25 | 80 |
| Ex. 3 | 1.25 | 0 | 0 |
|  | 1.25 | 0.25 | 100 |
| Ex. 4 | 1.25 | 0 | 0 |
|  | 1.25 | 0.25 | 80 |
| PBO | 1.25 | 0 | 0 |
|  | 1.25 | 0.25 | 60 |
| tetramethrin | 0 | 0.25 | 20 |

As can be seen from Table 1, all the compounds of the invention acted as synergists in respect of the tetramethrin, markedly increasing its insecticidal activity. All the compounds of the invention were better synergists of the insecticidal activity compared to the PBO. In particular, the compounds of examples 1 and 3 were the most active as synergists.

Example 6

Mortality Test of the Products of Examples 1 and 3 on Beetles

Solutions of products of examples 1 and 3 in acetone and, for comparison, of piperonyl butoxide, with the organic phosphorus compound chloropyriphos and with carbamate compound propoxur, were applied from a distance of 12 cm on glass plates (model Ostra, 15×15 cm=225 square cm) by means of a suitable glass sprayer so as to obtain an applied amount of organic phosphorous compound equal to 33 mg/square m and of carbamate equal to 500 mg/mq. The products of examples 1 e 3 and the comparison compound PBO were in a weight ratio of 5:1 w/w with respect to the organic phosphorous compound and to the carbamate.

In the same way acetone solutions of organic phosphorous compound and of carbamate compound were prepared so as to obtain an applied amount of organic phosphorous compound equal to 33 mg/square m and of carbamate compound equal to 500 mg/mq. After the application the plates were transferred to a closed test room under controlled temperature and humidity (24-25° C., RH 50-60%). Glass rings (h 5.5 cm×diameter 9.5 cm), having internal surface treated with talc and each one containing 5 beetles—*Blattella germanica*—were placed in the centre of the plates. They were evaluated each one after 1 day and three days from the application. For each day, the insects were maintained on the surface for 24 hours.

The results are reported in tables 2 and 3.

TABLE 2

| Prodotto | Conc. prodotto (mg/sm) | Conc. chloropyriphos (mg/sm) | Mortalità 1gg (%) | Mortalità 3gg (%) |
|---|---|---|---|---|
| Es. 1 | 165 | 33 | 62 | 85 |
| Es. 3 | 165 | 33 | 60 | 80 |
| PBO | 165 | 33 | 45 | 65 |
| Chloropyriphos | 0 | 33 | 32 | 48 |

TABLE 3

| Prodotto | Conc. prodotto (mg/sm) | Conc. propoxur (mg/sm) | Mortalità 1gg (%) | Mortalità 3gg (%) |
|---|---|---|---|---|
| Es. 1 | 2500 | 500 | 48 | 60 |
| Es. 3 | 2500 | 500 | 44 | 56 |
| PBO | 2500 | 500 | 35 | 42 |
| Propoxur | 0 | 500 | 20 | 31 |

It is evident from the above that the compounds of the invention were significantly more active than PBO when used also with a organic phosphorous compound and a carbamate compound.

The invention claimed is:

1. A 1,3-benzodioxole derivative compound of formula (I):

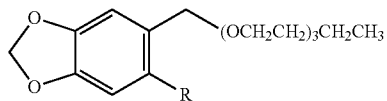

(I)

wherein R is a linear or branched ($C_4$-$C_{10}$)alkyl substituent as a synergistic compound of insecticidal active ingredients, wherein the insecticidal active ingredient is selected from the group consisting of pyrethroids, organic phosphorous compounds and carbamates.

2. The derivative compound according to claim 1, wherein R is a linear ($C_4$-$C_{10}$)alkyl substituent.

3. The derivative compound according to claim 2, wherein R is selected from the group consisting of n-butyl, n-hexyl, n-octyl and n-decyl.

4. The derivative compound according to claim 3, wherein R is n-octyl or n-hexyl.

5. An insecticidal composition comprising at least one insecticidal active ingredient and at least one synergistic compound of formula (I)

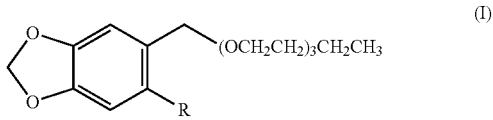

(I)

wherein R is a linear or branched ($C_4$-$C_{10}$)alkyl substituent, wherein the insecticidal active ingredient is selected from the group consisting of pyrethroids, organic phosphorous compounds and carbamates.

6. The composition according to claim 5, wherein R is a linear ($C_4$-$C_{10}$)alkyl substituent.

7. The composition according to claim 6, wherein R is selected from the group consisting of n-butyl, n-hexyl, n-octyl and n-decyl.

8. The composition according to claim 7, wherein R is n-octyl or n-hexyl.

9. The composition according to claim 5, wherein one or more synergistic compounds of formula (I) is comprised from 0.01% to 98% in a weight/weight percentage with respect to the total weight of the composition.

10. The composition according to claim 5, wherein said composition further comprises excipients selected from the group consisting of emulsifiers, UV-stabilizers and antioxidants.

11. An insecticidal formulation comprising the insecticidal composition according to claim 5 and carriers.

12. 5-[2-(2-butoxyethoxy)-ethoxymethyl]-6-n-octyl-1,3-benzodioxole

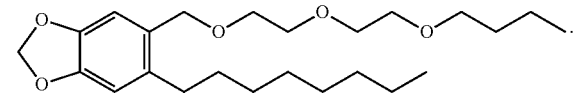 [SMILES: CCCCCCCCc1cc2c(cc1COCCOCCOCCCC)OCO2]

13. 5-[2-(2-butoxyethoxy)-ethoxymethyl]-6-n-decyl-1,3-benzodioxole)

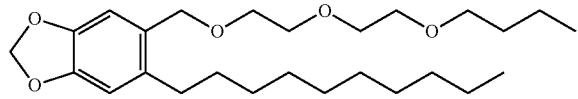 [SMILES: CCCCCCCCCCc1cc2c(cc1COCCOCCOCCCC)OCO2]

14. A method for eliminating insects which provides for applying an efficacy amount of the insecticidal composition according to claim 5 to substrates containing said insects.

15. A method for the treatment of insects comprising the step of applying the insecticidal composition of claim 5 on animals contaminated by insects.

* * * * *